(12) United States Patent
LoBiondo

(10) Patent No.: US 11,596,217 B1
(45) Date of Patent: Mar. 7, 2023

(54) COSMETIC CONTAINER

(71) Applicant: Paul LoBiondo, Sea Bright, NJ (US)

(72) Inventor: Paul LoBiondo, Sea Bright, NJ (US)

( * ) Notice: Subject to any disclaimer, the term of this patent is extended or adjusted under 35 U.S.C. 154(b) by 669 days.

(21) Appl. No.: 16/601,903

(22) Filed: Oct. 15, 2019

(51) Int. Cl.
    *A45D 40/22*      (2006.01)
    *A61K 8/27*      (2006.01)

(52) U.S. Cl.
    CPC ........ *A45D 40/22* (2013.01); *A45D 2200/155* (2013.01); *A61K 8/27* (2013.01)

(58) Field of Classification Search
    CPC .............. A45D 2200/155; B65D 23/12; B65D 47/0842; F25D 2331/803; F25D 2331/806
    See application file for complete search history.

(56) References Cited

U.S. PATENT DOCUMENTS

| | | | |
|---|---|---|---|
| 4,389,418 A * | 6/1983 | Burton | A61K 8/342 514/873 |
| 4,584,847 A | 4/1986 | Martello et al. | |
| 5,237,838 A * | 8/1993 | Merritt-Munson | F25D 3/08 383/110 |
| 6,415,624 B1 * | 7/2002 | Connors | F25D 31/007 62/530 |
| 7,857,155 B2 * | 12/2010 | Roberts | B65D 41/0485 220/254.3 |
| 2008/0230508 A1 * | 9/2008 | Overgaard | A45F 3/16 215/386 |

* cited by examiner

*Primary Examiner* — David P Angwin
*Assistant Examiner* — Bradley S Oliver
(74) *Attorney, Agent, or Firm* — Sanchelima & Associates, P.A.; Christian Sanchelima; Jesus Sanchelima

(57) ABSTRACT

A cosmetic container for storing cosmetic product is disclosed herein. The cosmetic container comprises a container having a thermal container receiving section. The cosmetic container further comprises a first end and a second end with the container including an opening at the second end used to store cosmetic product such as sunscreen therein. The second end of the cosmetic container also includes a neck portion comprising a threaded portion to receive a head. The cosmetic container further comprises a thermal container for storing a cooling agent. The thermal container is received in the thermal container receiving section for cooling down the cosmetic product stored in the container. When the thermal container is adapted onto the container, the product enclosed within the container is then cooled down. The cosmetic product thereby provides a cooling effect when applied on user's skin making the application of a cosmetic product a more comfortable action.

1 Claim, 3 Drawing Sheets

COSMETIC CONTAINER

BACKGROUND OF THE INVENTION

1. Field of the Invention

The present invention generally relates to cosmetic containers. More specifically, the present invention relates to a cosmetic container comprising a container and a thermal compartment mounted to the container for cooling down a cosmetic product contained in the container.

2. Description of the Related Art

It is known that cosmetic containers are used to store cosmetics, facial, hair care and beauty products. The cosmetic products may include, but not limited to, face cream, sunscreen lotion, skin care products, skin gel and so on. As known, the cosmetic products are used for improving the external beauty of a user, as they provide nutrients to the user's skin and retain moisture in the skin. Further, the cosmetic products block ultraviolet light from sun or air from being in direct contact with the skin and protect the user's skin. It is also known these products are best applied to a user's skin when at a cool temperature. The present invention addresses this cooling issue by providing a sunscreen comprising a gel-like substance for protecting human skin from UV rays, wherein the substance contains a combined cooling agent and a sunblock agent in a rigid plastic container that has an integrated freezer pack housed within the container. The freezer pack is a sealed cylindrical tube that contains a freezable substance.

Although the effectiveness of the cosmetic products depends on the ingredients used in the cosmetic products, manufacturers of the cosmetic products focus on design of the cosmetic containers in which the cosmetic products are stored. It is well documented that the using cosmetic products at a low temperature provides a moist and refreshing feel to the user and results in cooling down of the body. Several attempts have been made in the past to provide cooling devices for cosmetics. One such example is disclosed in a U.S. Pat. No. 4,584,847. In U.S. Pat. No. 4,584,847A, a new instant cooling device for cosmetics is disclosed. Unique light weight and small refrigerator system is used in combination with a safety device to reinstate the proper hardness and consistency of facial cosmetics by cooling. The instant cooling device comprises pressure vessel with valve containing liquid refrigerant and adequate release mechanism to allow efficient cooling of personal size cosmetics. However, the reference disclosed is provided in unnecessarily complex and inefficient way. The disclosure fails to address the issue of providing a user with an efficient and effortless system to keep a user's cosmetic products cool. The present invention addresses these issues by providing a cosmetic container having a thermal container receiving section. The thermal container receiving section is adapted to receive a thermal container that is configured to keep cosmetics stored within cool in an effortless and efficient manner.

Other documents describing the closest subject matter provide for a number of more or less complicated features that fail to solve the problem in an efficient and economical way. None of these patents suggest the novel features of the present invention. Specifically, none of the disclosures in the art disclose a cosmetic container comprising a container and a thermal compartment mounted to the container for cooling down a cosmetic product contained in the container.

Therefore, there is a need in the art for a cosmetic container comprising a container and a thermal compartment removably mounted to the container for cooling down a cosmetic product contained in the container.

SUMMARY OF THE INVENTION

It is one of the objects of the present invention to provide a cosmetic container for storing cosmetic product and that avoids the drawbacks of the prior art.

It is one object of the present invention to provide a cosmetic container comprising a container and a thermal container storing a cooling agent. The thermal container when mounted to the container storing cosmetic product reduces the temperature of the cosmetic product thereby creating a cooling effect to a user applying said cosmetic product.

It is one object of the present invention to removably mount the thermal container to a container storing cosmetic product for cooling the cosmetic product thereby creating an efficient system for cooling multiple cosmetic products.

It is one object of the present invention to provide a cosmetic container for storing cosmetic product at a low temperature, and when applied on user's skin which allows the user to stay cool and comfortable in sun and hot temperatures.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

The following detailed description is intended to provide example implementations to one of ordinary skill in the art, and is not intended to limit the invention to the explicit disclosure, as one or ordinary skill in the art will understand that variations can be substituted that are within the scope of the invention as described.

Figure 1:
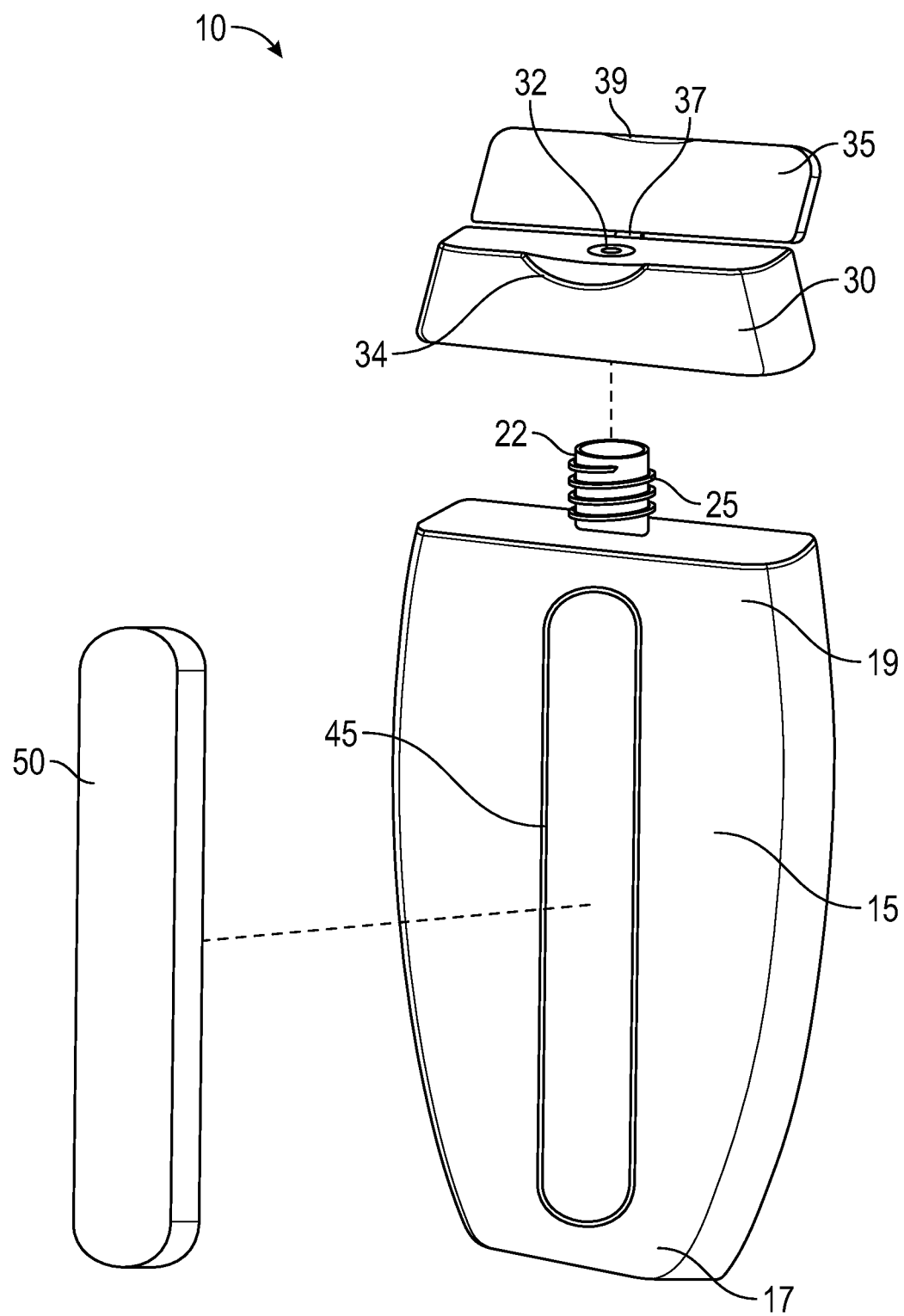
FIG. 1 illustrates an exploded view of a cosmetic container 10, in accordance with one embodiment of the present disclosure wherein a container 15, a head 35, and a thermal container 50 may be observed.
Figure 2:
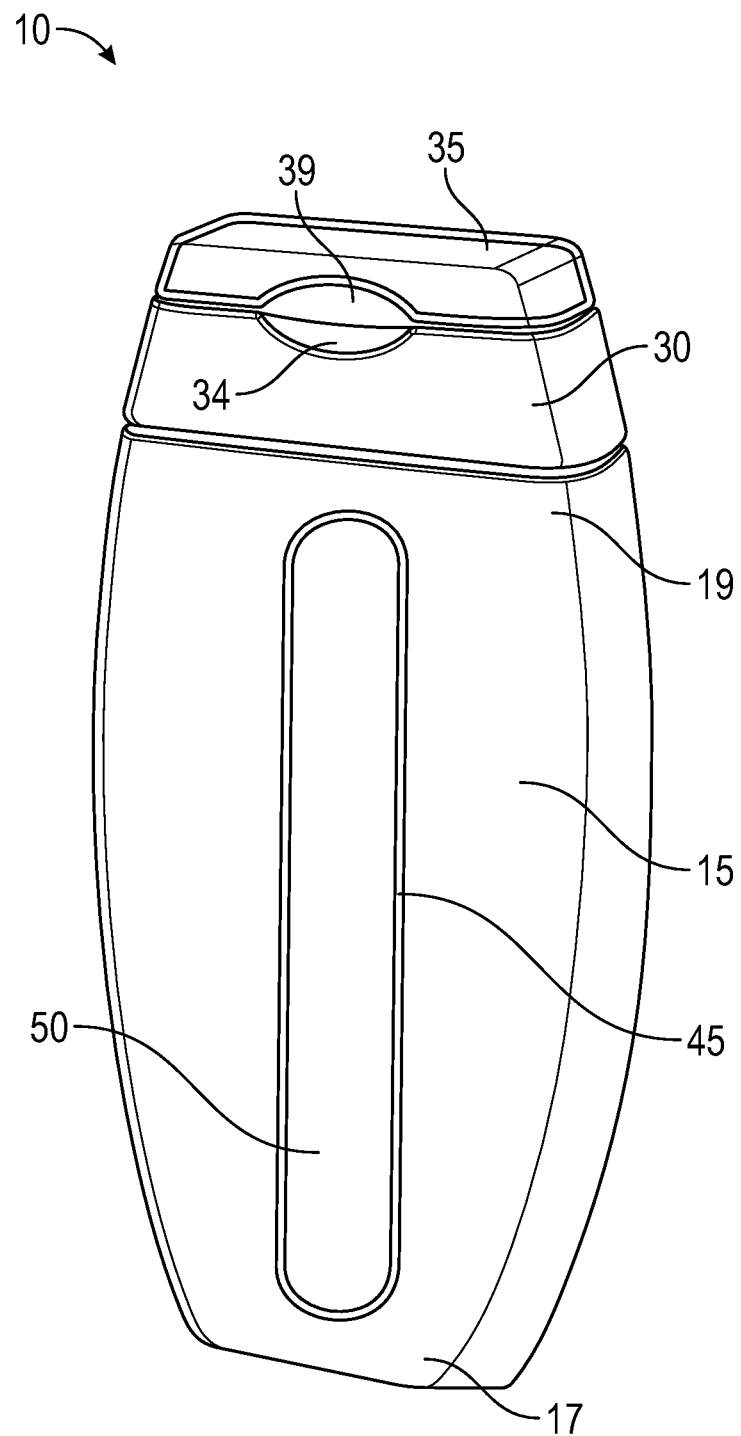
FIG. 2 depicts an isometric view of said cosmetic container 10, wherein said thermal container 50 is seen attached to said container 15 through means of thermal container receiving section 45.
Figure 3:
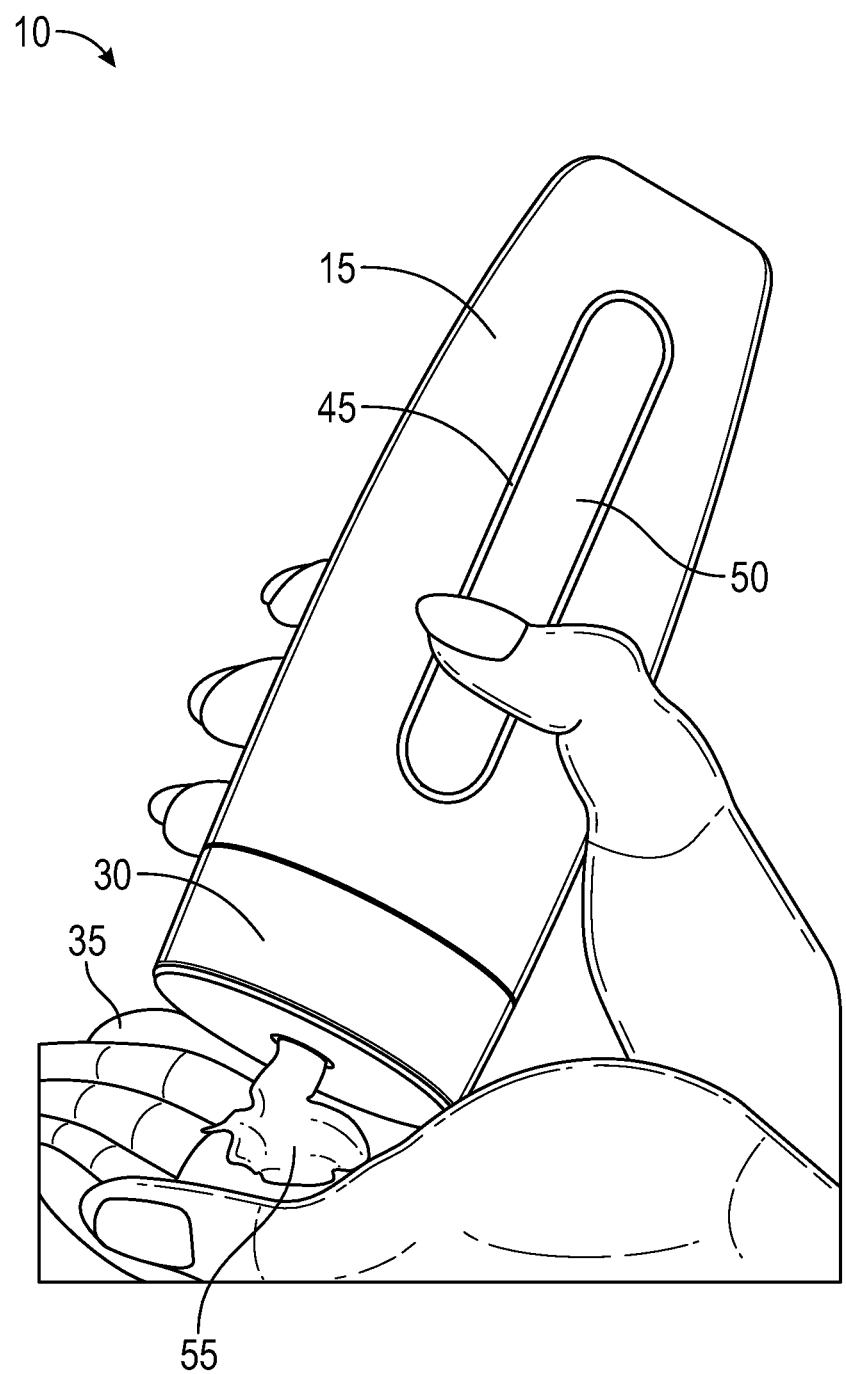
FIG. 3 illustrates cosmetic product 55 being dispensed from the cosmetic container 10, in accordance with one embodiment of the present disclosure.

Various features and embodiments of a cosmetic container are explained in conjunction with the description of FIGS. 1-3.

Referring to FIG. 1, an exploded view of a cosmetic container 10 is shown, in accordance with one embodiment of the present disclosure. The cosmetic container 10 comprises a container 15. The container 15 may indicate a bottle, box, case, tube and so on. The container 15 might be made up of a high density plastic or any other suitable material. The container 15 might be provided in variety of shapes and sizes. In one example, the container 15 might be provided in cylindrical shape. In another example, the container 15 might be provided in oval shape with flat base. In another example, the container 15 might be provided in a curved shape with flat base.

The container 15 may comprise a first end 17 and a second end 19. The first end 17 might indicate a bottom end of the container 15. The second end 19 might indicate a top end of the container 15. At the second end 19, the container 15 may comprise a neck portion 22. It should be understood that the neck portion 22 might be provided either as an integral part of the container 15 or as a separate part from that of the container 15. The neck portion 22 may comprise a threaded portion 25 on its surface.

Further, the cosmetic container 10 comprises a head 30 removably mounted to the container 15 via the neck portion 22. The head 30 may comprise internal threading which is used to mount to the neck portion 22 at the threaded portion 25. Further, the head 30 may comprise an opening 32 provided in alignment with the neck portion 22 such that product stored in the container 15 is made to come out through the opening 32 when pressure is exerted on the container 15. In one example, the head 30 may be provided with a first recess portion 34 for allowing a user to have grip while holding the head 30.

Further, the cosmetic container 10 comprises a cap or lid 35 mounted to the head 30 using a hinge 37. Further, the cap 35 comprises a second recess portion 39, which allows the user to operate the cap 35.

In one implementation, the container 15 is provided with a thermal container receiving section 45. It should be understood that the thermal container receiving section 45 might be provided at one of the sides of the container 15. The thermal container receiving section 45 might be provided in variety of shapes and sizes. It should be understood that the thermal container receiving section 45 might be formed by cutting a portion of the container 15 or by molding the container 15 to include the thermal container receiving section 45, as shown in FIG. 1.

Further, the cosmetic container 10 is provided with a thermal container or freezer pack 50. The thermal container 50 might be provided as a sealed cylindrical tube made up of plastic or fabric or synthetic or polyethylene, or paper or any other suitable material. As can be seen in FIG. 1, the thermal container 50 is provided in the shape of the thermal container receiving section 45, such that the thermal container 50 is mountable to the container 15 at the thermal container receiving section 45.

Referring to FIG. 2, the head 30 mounted to the container 15 at the neck portion 22 is shown. As specified above, the cap 35 is mounted to the head 30 using the hinge 37. As such, the cap 35 can be operated to close the opening 32 of the head 30. Further, the thermal container 50 is mounted to the container 15 at the thermal container receiving section 45.

Referring to FIG. 3, the container 15 might be used to store a cosmetic product 55. The cosmetic product 55 may include, but not limited to, face cream, sunscreen lotion, skin care products, skin gel and so on. In accordance with one exemplary embodiment, the container 15 is used to store the cosmetic product 55 i.e., sunscreen in gel form. However, it should be understood that the cosmetic product 55 might be used to other forms such as cream or foam form. In one example, the cosmetic product 55 might be formulated to block sunlight and to provide a cooling effect to a user when applied. In one example, the cosmetic product 55 might be using ingredients such as menthol, oxybenzone and zinc oxide. In the above example, menthol may act a cooling agent and oxybenzone and zinc oxide may block ultraviolet rays when applied on the user's skin. It should be understood that the above composition is used for exemplary purpose; other compositions may also be used to provide cooling effect when applied to the user's skin.

Further, the thermal container 50 might be provided with a cooling agent or cooling substance that is kept in frozen state inside the thermal container 50. In one example, the thermal container 50 might be permanently mounted to the container 15 such that the thermal container 50 will be disposed off along with the container 15 once the cosmetic product 55 is used up. In another example, the thermal container 50 might be removably mounted to the container 15 such that the thermal container 50 can be reused with another container 15, or the cosmetic product 55 can be refilled into the container 15 for longer use.

It should be understood that when the thermal container 50 filled with cooling agent is mounted to the container 15, the walls of the container 15 comes in contact with the thermal container 50 and gets cold. Further, the cosmetic product 55 contained in the container 15 gets cold. As such, when the user squeezes the container 15, the cosmetic product 55 at a low temperature is dispensed which provides a moist and refreshing feel to the user and results in cooling down of the body when applied on the user's skin.

In another embodiment of the present invention, container 15 may be in the form of a can. The can may further include thermal container receiving section 45 that is configured to received thermal container 50. Additionally, it should be understood that head 30 may come in the form of a spraying attachment head, configured to spray the product therein when used by a user.

Based on the above, it is evident that the cosmetic container can be used to store cosmetic product at a low temperature, and when applied on user's skin which allows the user to stay cool and comfortable in sun and hot temperatures. It should be understood that the cosmetic product could be provided in variety of forms such as cream, gel-like substance.

The cosmetic product can be make up ingredients such as menthol, oxybenzone and zinc oxide to provide cooling effect and to protect from ultraviolet rays, however a person skilled in the art will understand that other materials in different composition may also be used to make the cosmetic product.

The cosmetic container can be provided in various shapes and sizes depending upon the need.

Although it is explained considering that the cosmetic container is used to store cosmetic product, it should be understood that the cosmetic container could be used to store another products at a low temperature based on the explanation provided above.

The drawings shown herein are provided for illustrative purpose only, and shape and size of each components illustrated should not be construed in limited sense. A person skilled in the art will appreciate that components may be added or deleted to incorporate additional features described in the present disclosure and even such disclosures will be within the scope of the present disclosure.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A system for a cosmetic container, consisting of:
    a. a container having a volumetric ellipse shape with truncated ends, wherein said truncated ends are composed by a first end and a second end said container having a neck portion located at said second end of said container, said container further includes a thermal container receiving section that is volumetrically suitable to removably receive a thermal container therein, said thermal container receiving section having two straight lateral sides with a concave top side and a u-shaped bottom side, said thermal container receiving section is aligned with said neck portion, said thermal container receiving section is disposed upon a front surface of the container, said neck portion has a threaded portion about an external surface thereof, said neck portion has a cylindrical shape centrally disposed that extends upwardly from the second end, wherein the container stores a cosmetic product, the cosmetic product is made using menthol and zinc oxide;
    b. the thermal container for storing a cooling agent, wherein the thermal container is received in the thermal container receiving section for cooling down the cosmetic product stored in the container, and wherein the cosmetic product provides a cooling effect when applied on user's skin, said thermal container is evenly flush and abutting with an interior surface of the thermal container receiving section, said thermal container is configured to cool the cosmetic product by conduction;
    c. a head is removably secured to said neck by means of said threaded portion, said head further includes a cap hingedly attached at a periphery thereof, said head includes an opening that is aligned to said neck to permit said cosmetic product to be expelled therethrough.

* * * * *